United States Patent [19]
Pellegrino et al.

[11] Patent Number: 5,594,769
[45] Date of Patent: Jan. 14, 1997

[54] METHOD AND APPARATUS FOR OBTAINING STEREOTACTIC MAMMOGRAPHIC GUIDED NEEDLE BREAST BIOPSIES

[75] Inventors: Anthony J. Pellegrino, New Fairfield, Conn.; Kenneth F. DeFreitas, Patterson, N.Y.

[73] Assignee: Thermotrex Corporation, San Diego, Calif.

[21] Appl. No.: 437,793

[22] Filed: May 9, 1995

Related U.S. Application Data

[60] Continuation-in-part of Ser. No. 388,810, Feb. 15, 1995, which is a division of Ser. No. 185,690, Jan. 24, 1994, Pat. No. 5,426,685, which is a division of Ser. No. 957,275, Oct. 6, 1992, Pat. No. 5,289,520, which is a continuation-in-part of Ser. No. 799,412, Nov. 27, 1991, abandoned.

[51] Int. Cl.⁶ ........................................... A61B 6/04
[52] U.S. Cl. ............................ 378/37; 378/208; 128/754
[58] Field of Search ........................... 378/37, 205, 208, 378/65; 128/653.1, 662.05, 754

[56] References Cited

U.S. PATENT DOCUMENTS

| | | | |
|---|---|---|---|
| 3,609,355 | 9/1971 | Schwarzes | 250/50 |
| 4,727,565 | 2/1988 | Ericson | 378/205 |
| 4,875,478 | 10/1989 | Chen | 128/303 |
| 4,930,143 | 5/1990 | Lundgren et al. | 378/37 |
| 5,018,176 | 5/1991 | Romeas et al. | 378/37 |
| 5,050,197 | 9/1991 | Virta et al. | 378/37 |
| 5,056,523 | 10/1991 | Hotchkiss, Jr. et al. | 128/653 |
| 5,078,142 | 1/1992 | Siczek et al. | 128/653.1 |
| 5,107,843 | 4/1992 | Aarnio et al. | 128/662.05 |
| 5,213,100 | 5/1993 | Summ | 128/653.1 |
| 5,386,447 | 1/1995 | Siczek | 378/37 |
| 5,539,797 | 7/1996 | Heidsieck et al. | 378/37 |

OTHER PUBLICATIONS

Björn Nordenström, M. D. Hakan Ryden, M. Se.; Gunilla Svane, M. D. "Breast" Chapter 5 of Percutanious Needle Biopsy (Wms & Winkins Co. 1981, J. Zornoza.

Björn Nordenström, M. D.; "Stereotaxic Screw Needle Biopsy of Nonpalpable Breast Lesions"; Breast Caroinoma, the Radiologist's Expanded Role; (John Wiley 1977, W. W. Gogan, ed.).

TRC *Mammotest* (Diagnostic System for Breast Cancer) Jan Bolmgren, Bertil Jacobson and Björn Nordenstöm "Stereotaxic Instrument for Needle Biopsy of the Mamma ".

*Primary Examiner*—Don Wong
*Attorney, Agent, or Firm*—Ware, Fressola, Van Der Sluys & Adolphson

[57] ABSTRACT

An add-on biopsy apparatus attached to a conventional mammography apparatus permits stereotactic imaging of a breast held in a mammographic position using an image receiver having a plane positioned perpendicular to the X-ray source. The perpendicularly positioned image plane allows the use of conventional moving scatter reducing grids to improve image contrast and quality of a stereotactic image made with an add-on biopsy apparatus. The biopsy apparatus also includes a control system for position a digital image receiver to compensate for image shifting during stereotactic imaging.

9 Claims, 11 Drawing Sheets

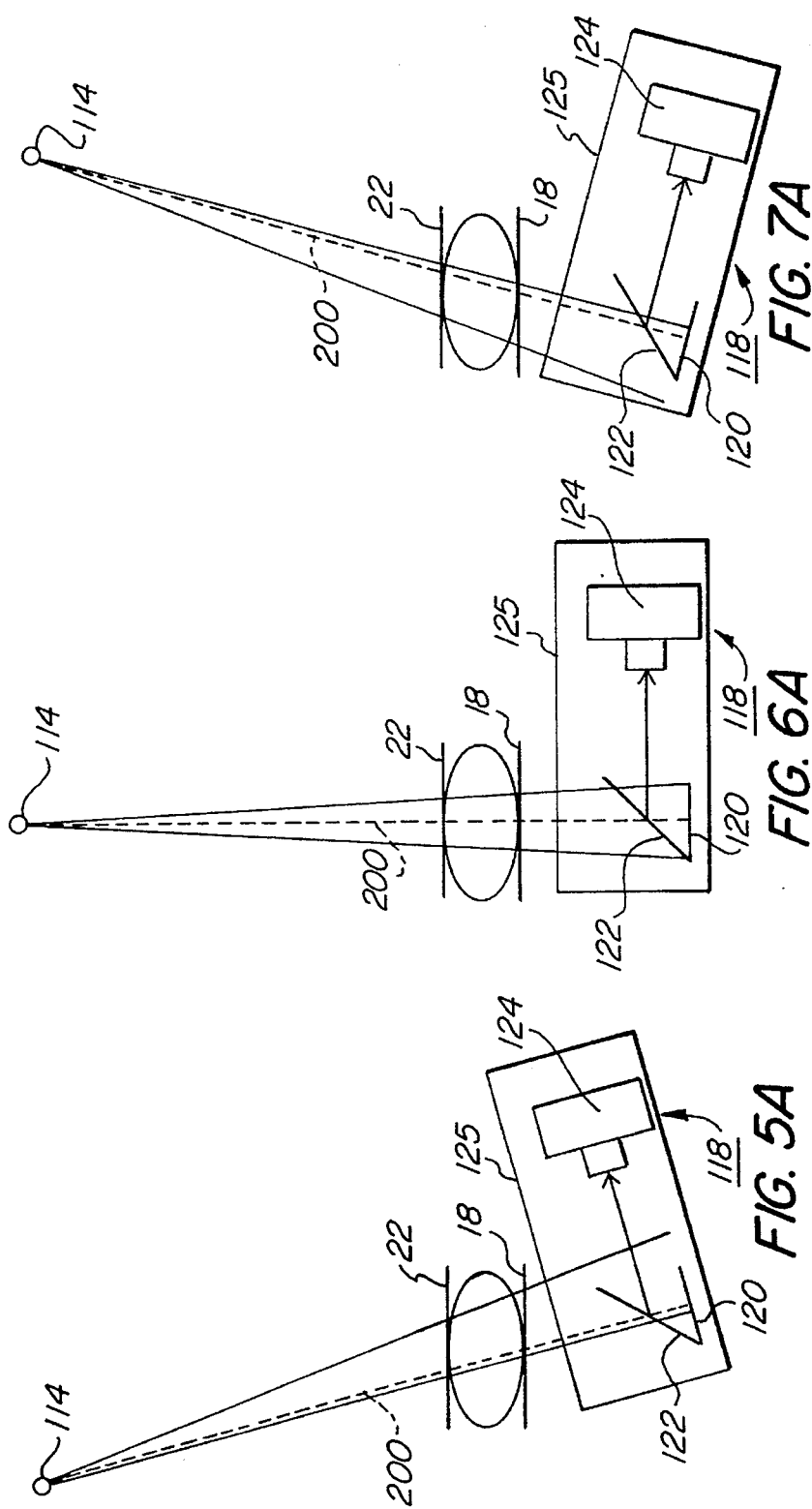

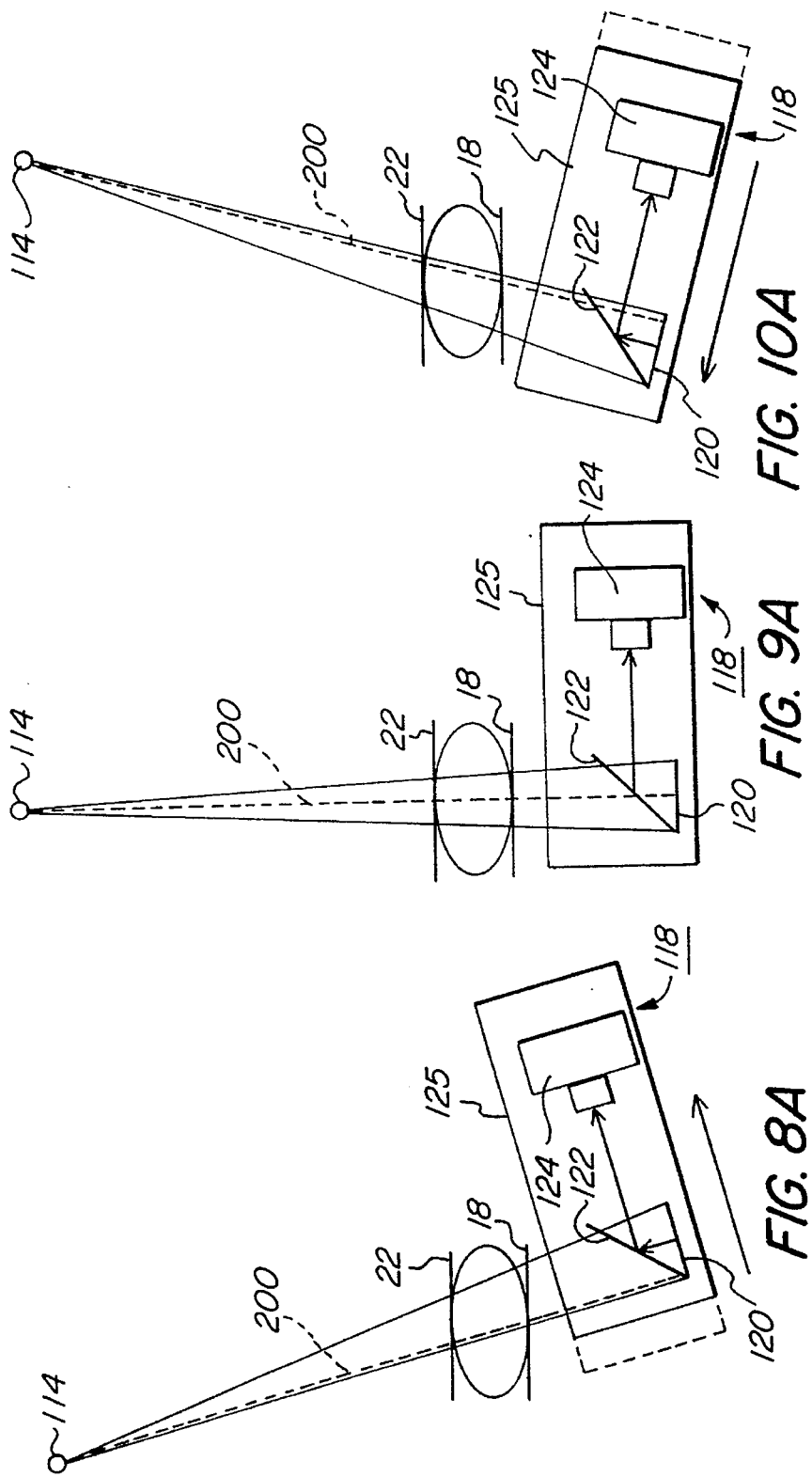

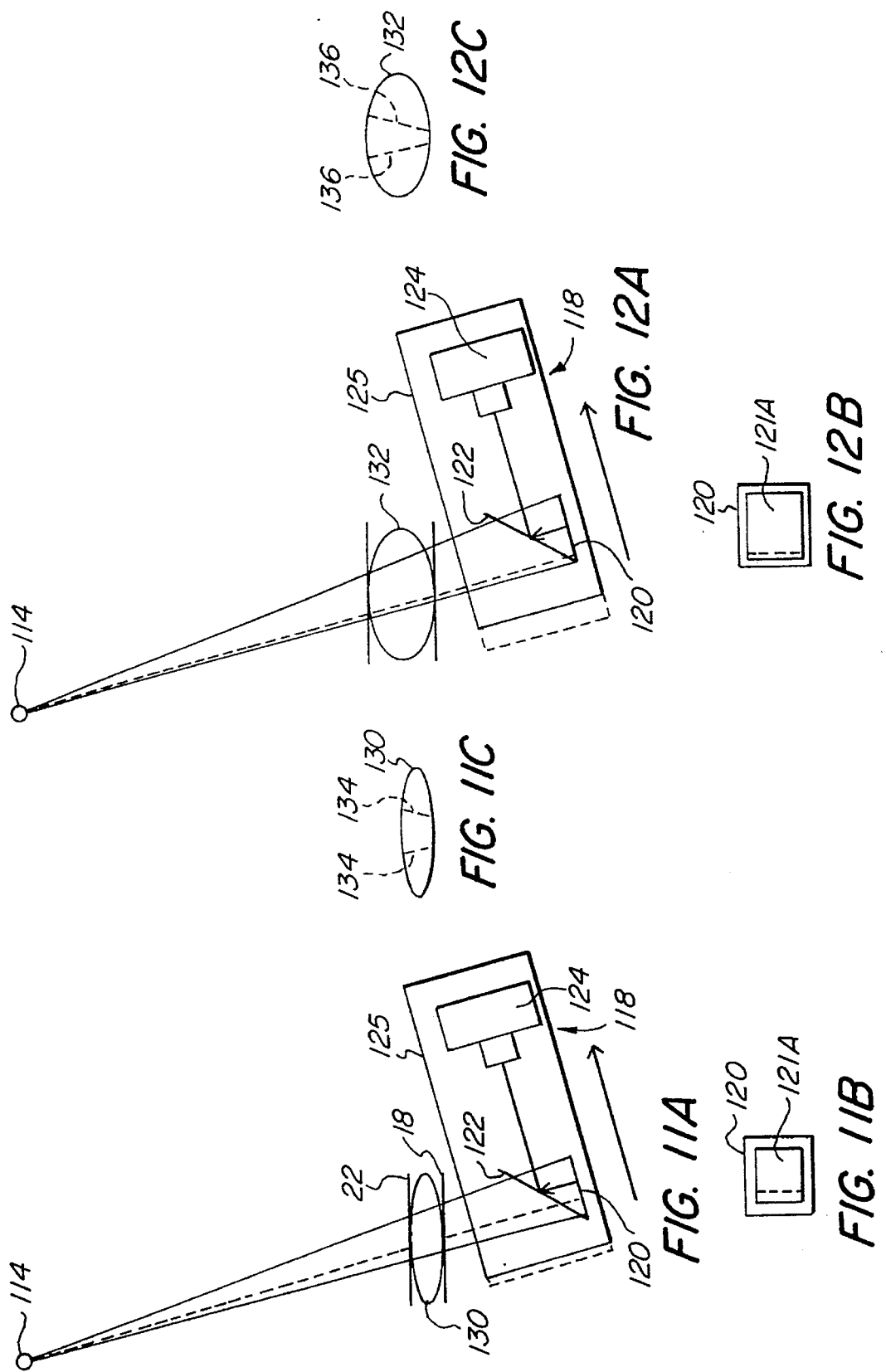

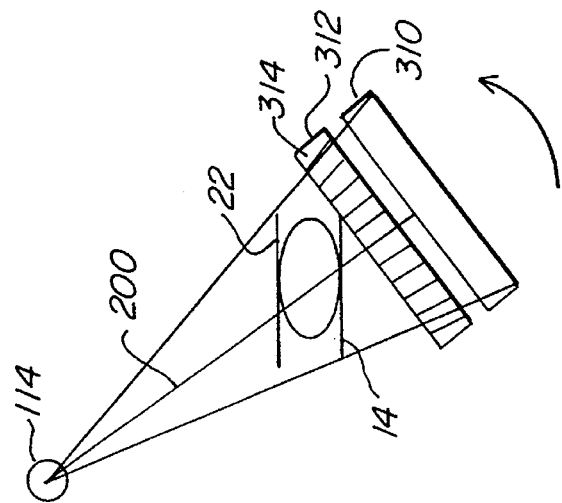
FIG. 16C
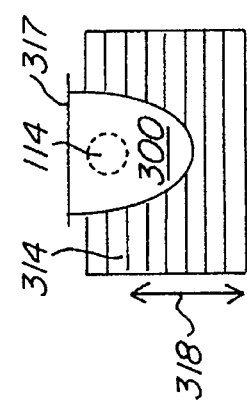
FIG. 19
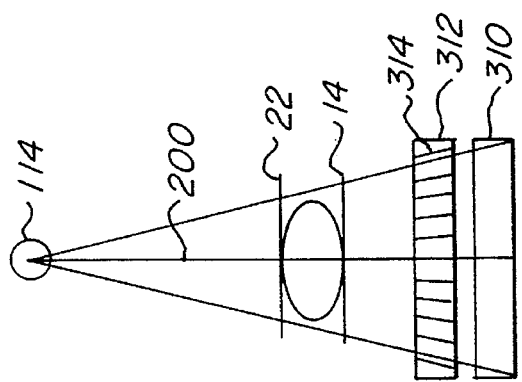
FIG. 16B
FIG. 18
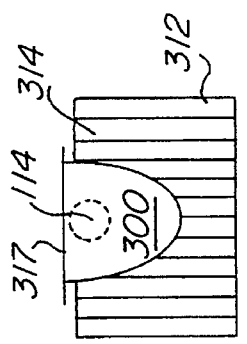
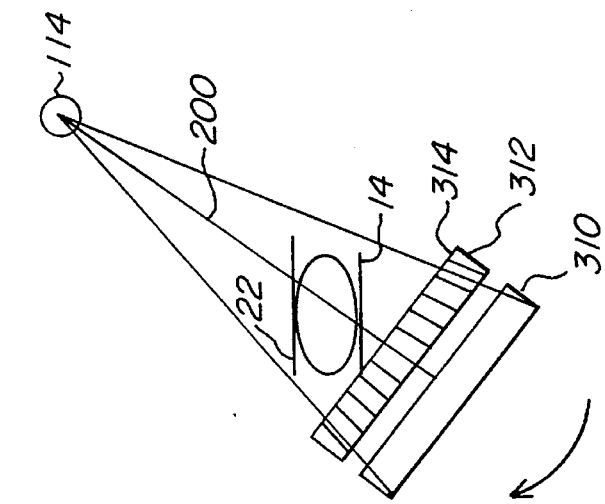
FIG. 17
FIG. 16A
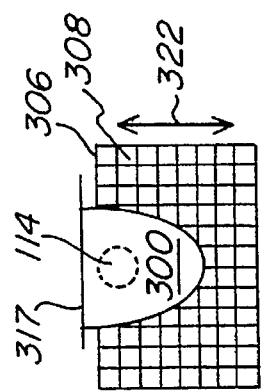

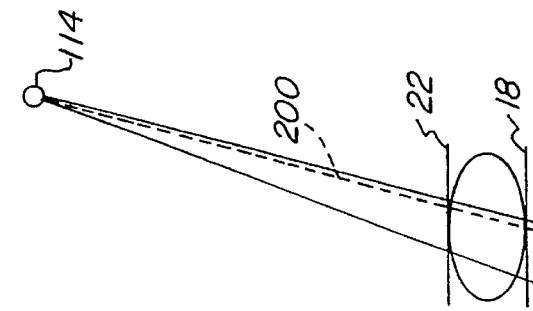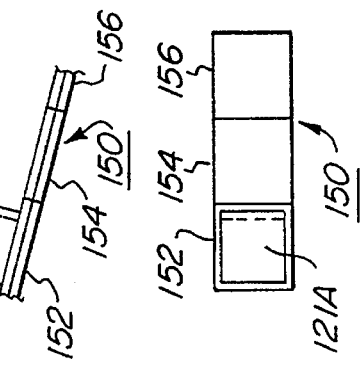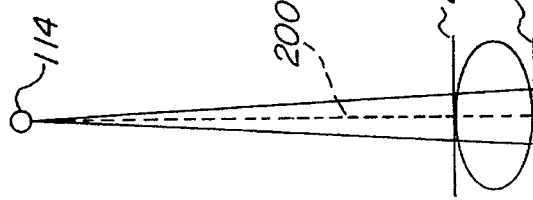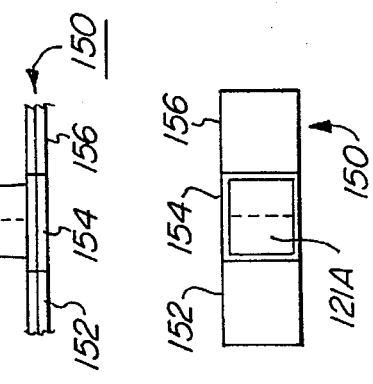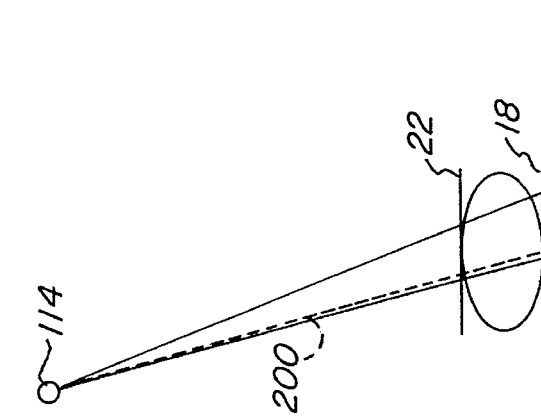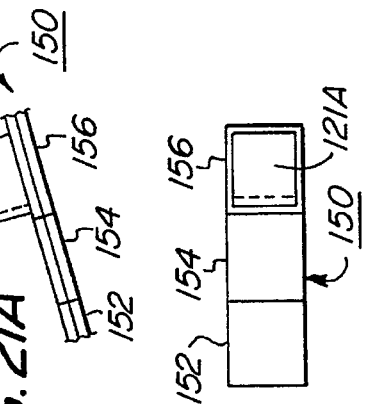

METHOD AND APPARATUS FOR OBTAINING STEREOTACTIC MAMMOGRAPHIC GUIDED NEEDLE BREAST BIOPSIES

CROSS REFERENCE TO RELATED APPLICATIONS

This is a continuation-in-part of Ser. No. 08/388,810 filed on Feb. 15, 1995 which is a divisional application of Ser. No. 08/185,690 filed on Jan. 24, 1994, now U.S. Pat. No. 5,426,685 which is a divisional application of Ser. No. 07/957,275 filed on Oct. 6, 1992, now U.S. Pat. No. 5,289,520, issued on Feb. 22, 1994, which is a continuation-in-part of Ser. No. 07/799,412, filed Nov. 27, 1991, now abandoned.

BACKGROUND OF THE INVENTION

1. Field of the Invention

The present invention generally relates to stereotactic mammographic guided needle breast biopsies, and more particularly to an add-on stereotactic needle breast biopsy apparatus for converting a conventional mammography apparatus into a mammography apparatus capable of taking high quality stereotactic mammographic images of a breast and performing stereotactically guided needle breast biopsies on lesions identified in the stereotactic images.

2. Description of the Prior Art

Within the last couple of decades there have been many improvements made in the field of mammography and stereotactic mammographic guided needle breast biopsies. These improvements have allowed the field to move towards faster, more accurate and less invasive procedural techniques to determine whether a suspicious lesion spotted in a mammographic image is malignant. More particularly, the field of mammography, as with many other medical imaging procedures, is shifting from traditional screen-film based imaging, where mammographic images are captured on a film negative, to digital imaging, where such images are acquired on a Charge Coupled Device (CCD) array and displayed on a cathode ray tube (CRT). While the advantages of the latter method for imaging are numerous, one of the most readily notable advantages is the significant reduction in image acquisition time. For example, an image captured on a CCD array may be displayed on a CRT in as little as three to six seconds after the mammographic imaging procedure is completed. In contrast, it can take more than 5 to 10 minutes to obtain the same image captured on a film negative due to processing time requirements involved in developing the mammogram film negative. The reduction in image acquisition time has been a real benefit to patients undergoing a stereotactically guided needle breast biopsy. An example of a digital imaging camera system employing a CCD array which is suitable for use in mammography may be found in the applicants' U.S. Pat. No. 5,216,250, which is incorporated herein by reference in its entirety.

Stereotactic mammographic guided needle breast biopsy procedures are evolving towards sampling cells of suspicious lesions through less invasive fine needle aspiration (FNA) procedures and sampling tissue of suspicious lesions through needle core biopsies, and away from using more invasive procedures, such as wire guided surgical excision of the suspicious lesion. Generally, there are two types of stereotactic mammographic guided needle breast biopsy devices, add-on and dedicated, described in the art for performing the range of stereotactically mammographic guided needle breast biopsies described above.

A prior art add-on biopsy device allowing stereotactic mammographic breast biopsy procedures to be carded out using a conventional mammography apparatus is disclosed in U.S. Pat. No. 4,727,565. The add-on biopsy device described therein comprises a needle guiding stage, a compression paddle and an image receiver. When a stereotactic guided needle biopsy is desired, the biopsy device is attached to a conventional mammography device. The patient's breast is held in a compressed state between the compression paddle and image receiver. To acquire the stereotactic images, the device employs oblique angle stereotactic imaging geometry wherein the X-ray tube of the mammography apparatus is positioned at oblique angles relative to the plane defined by the image receiver. Once the stereotactic images are obtained, the two dimensional positional coordinates of the suspicion lesion appearing in each of the images is measured and these two dimensional positional coordinates are used to calculate the three dimensional coordinates of the suspicious lesion in the breast relative to the needle guiding stage. Unfortunately, the oblique angle stereotactic imaging geometry employed by this device to acquire stereotactic images has some drawbacks which can possibly compromise the image quality of the stereotactic images. The imaging geometry drawbacks will be more fully explained below.

A prior art dedicated biopsy device for carrying out stereotactic mammographic breast biopsy procedures is described in "Stereotaxic Instruments for Needle Biopsy of the Mamma", an article authored by Jan Bolmgren et al, published in the American Journal of Roentgenology, Vol. 129, page 121, in July 1977. In the dedicated biopsy device, the patient is positioned on a table in a prone position over the imaging and biopsy apparatus. The breast is pendulantly presented through an aperture at one end of the table. The obvious advantage of the dedicated biopsy device over the add-on biopsy device is that it is far more comfortable for the patient. However, the dedicated biopsy device tends to be relatively more expensive and tends to take up more floor space, which, in some situations, can also be expensive. Typically, the dedicated device is only used for stereotactic mammographic breast biopsy procedures so it may have somewhat less overall utility than a conventional mammography device equipped with an add-on stereotactic biopsy apparatus. A commercial version of this device, known as a TRC Mammotest was manufactured by Tekniska Roontgencentralen AB of Sweden. A description of the commercial TRC Mammotest may be found in U.S. Pat. No. 5,078,142. The two dedicated devices identified herein also suffer from the same oblique angle stereotactic imaging geometry drawbacks as mentioned above for the prior art add-on device.

While there is little doubt that oblique angle stereotactic imaging geometry, briefly described in the '565 patent, is sufficient for calculating the three dimensional coordinates of an observed lesion in a pair of images, it is believed that this stereotactic imaging geometry is not the best for obtaining stereotactic images with optimum image quality, quality approaching that of conventional screening mammography. More particularly, because these devices position the X-ray tube at an oblique angle relative to the plane of the image receiver for each of the stereotactic images, it is nearly impossible to use a conventional moving scatter reducing grid in a conventional manner because the central ray of the X-ray beam does not fall normal to the plane of the image receiver.

Conventional scatter reducing grids generally comprise a plurality of nearly parallel slats of X-ray absorbing materials that are typically positioned to be focused at the focal spot of the X-ray tube. These grids are also moved in a direction tangential to the patient's chest wall during the X-ray exposure to blur the shadows cast on the film by the plurality of X-ray absorbing materials. Because the central ray of the X-ray beam of the above described prior art devices is not presented normal or perpendicular to the plane of the X-ray film in either of the stereotactic imaging positions, it is nearly impossible to use a moving scatter reducing grid in the conventional manner because the oblique angle stereotactic X-ray imaging positions take the focal point of the X-rays outside of the focus of the grid. While it is possible that one skilled in the art could orient a conventional grid such that it could be used during stereotactic imaging with these prior art devices to somewhat overcome the above described constraints, these prior art biopsy devices have a further drawback in that they cannot use scatter reducing grids having X-ray absorbing materials arranged in a crossed structure because there is no way to orient the grid in the image plane such that this type of grid will be in focus with the focal spot of the X-ray tube during stereotactic imaging.

Thus, it is possible that a suspicious lesion spotted in a mammogram obtained by standard screening mammography techniques using a conventional scatter reducing grid may not be observable in stereotactic images taken with these prior art devices because they are generally unable to effectively use the scatter reducing grids. A brief discussion of the benefits of scatter reducing grids may be found in the Recommended Specifications for New Mammography Equipment published by the American College of Radiology.

The above noted limitations of the oblique angle imaging geometry of the prior art add-on and dedicated devices have been overcome by the stereotactic mammography imaging system described in related grandparent U.S. Pat. No. 5,289,520, which is incorporated herein by reference in its entirety. The device disclosed therein is a dedicated stereotactic mammography biopsy system. It overcomes the oblique angle imaging limitations by obtaining stereotactic images of the breast with perpendicular stereotactic imaging geometry wherein the focal spot of the X-ray tube is always presented normal to the plane of the X-ray film in each of the stereotactic imaging positions. Unlike the oblique angle stereotactic imaging geometry of the prior art devices, the perpendicular stereotactic imaging geometry does not place the same constraints on the use of scatter reducing grids since the X-ray focal spot remains in the same position relative to the image receiver during all stereotactic imaging. Thus, a conventional scatter reducing grid will always be in focus with the focal spot of the X-ray tube during all stereotactic imaging. However, while this device is more comfortable for the patient, as explained above, dedicated biopsy devices may have somewhat less overall utility for the user and can be more expensive than a typical mammography-apparatus equipped with an add-on type stereotactic needle biopsy device.

For at least several years, some mammography apparatus have been equipped with digital image receivers having a CCD camera focused through an optical arrangement of mirrors and lens or optical fibers at a phosphor screen. As compared to film-screen image receivers, digital image receivers tend to have a small field of view due to the costs of CCD arrays. When a mammography apparatus equipped with a digital image receiver having the small field of view is used to acquire stereotactic images and perform needle biopsies, conditions can arise such that the resulting stereotactic X-ray images do not completely fall within the field of view of the CCD camera. Accordingly, it is possible that a lesion in some of the stereotactic X-ray images can fall outside of the field of view in one or even both stereotactic images.

SUMMARY OF THE INVENTION

The present invention overcomes the drawbacks of the prior art by providing a biopsy apparatus for performing stereotactic mammographic needle biopsies on a breast with a conventional mammography apparatus that can obtain images with either a digital image receiver or a conventional film-screen image receiver. The mammography apparatus that may be used with the biopsy apparatus generally includes a base, a pivot shaft connected to the base at a first end, and a second end, the pivot shaft further defining a pivot axis, an imaging arm having an X-ray source end and an X-ray receiving end, the imaging arm being attached to the second end of the pivot shaft at a point between the X-ray source end and the X-ray receiving end, an X-ray tube having a focal spot, the X-ray tube being connected to the imaging arm at its X-ray source end, an X-ray image receiver support affixed to the imaging arm at its X-ray receiving end, and an X-ray image receiver attached to the support.

The biopsy apparatus for performing stereotactic mammographic needle biopsies with the conventional mammography apparatus described above includes a biopsy apparatus base which has first and second sides and a compression plate engaging end. A compression plate is attached to the biopsy apparatus base at the compression plate engaging end. A multi-dimensional positionable biopsy needle guiding stage is attached to the first side of the biopsy apparatus base and a biopsy needle holder is connected to the needle guiding stage. The biopsy apparatus also includes a compression paddle carriage slidably attached to the biopsy apparatus base on its first side between the biopsy needle guiding stage and the compression plate and a compression paddle, having an opening therein permitting a biopsy needle to be inserted into a breast, is affixed to the compression paddle carriage. A breast is held in position between the compression paddle and compression plate during imaging and the biopsy procedure. The biopsy apparatus further includes a pivot member having first and second ends. The first end of the pivot member is pivotally attached to the second side of the biopsy apparatus base near its compression plate engaging end and the pivotally attached pivot member allows pivotal motion of the biopsy apparatus base relative to the imaging arm of a conventional mammography apparatus having an imaging arm which pivots about a pivot axis defined by a pivot shaft of the mammography apparatus. The pivot member of the biopsy apparatus also includes a means for attaching the biopsy apparatus to the imaging arm, the means being affixed to the pivot member at its second end.

Accordingly, it is one object of the present invention to provide an add-on stereotactic needle biopsy apparatus to convert a conventional mammography apparatus into a device for carrying out stereotactic mammographic guided needle breast biopsies.

It is another object of the present invention to provide an add-on stereotactic needle biopsy apparatus for a conventional mammography apparatus that can use scatter reducing grids in the conventional manner to improve the image quality of stereotactic images.

It is another object of the present invention to provide an add-on stereotactic needle biopsy apparatus for a conventional mammography apparatus equipped with a digital image receiver.

These objects are accomplished, at least in part, by providing an add-on stereotactic biopsy apparatus that obtains stereotactic images using perpendicular stereotactic imaging geometry.

These objects are also accomplished, at least in part, by shifting the position of a digital image receiver during stereotactic imaging in proportion to the thickness of the object being imaged.

These objects are further accomplished, at least in part, by acquiring stereotactic images with a scatter reducing grid.

Other objects and advantages of the present invention will become apparent to those skilled in the art from the following derailed description read in conjunction with the attached drawings and claims appended hereto.

BRIEF DESCRIPTION OF THE DRAWINGS

The drawings, not drawn to scale, which include:

FIGS. 5A, 5B, 6A, 6B, 7A and 7B are a series of schematic diagrams illustrating the problem of image shifting during stereotactic imaging using the existing perpendicular stereotactic imaging geometry of a typical mammography apparatus and a collimating stainless steel needle biopsy compression paddle;

FIGS. 8A, 8B, 9A, 9B, 10A and 10B are a series of schematic diagrams illustrating the repositioning of the image receiver to solve the problem of image shifting during stereotactic imaging with a collimating stainless steel needle biopsy compression paddle;

FIGS. 11A, 11B, 11C, 12A, 12B and 12C are a series of schematic diagrams illustrating that the degree of shift is proportional to the thickness of the breast being imaged and biopsied;

FIGS. 16A, 16B and 16C are a series of schematic front elevation diagrams illustrating the relative position of the X-ray absorbing grid structures of a conventional X-ray scatter reducing grid oriented in a conventional manner relative to the X-ray tube in the perpendicular stereotactic imaging geometry employed by the present invention;

FIGS. 17, 18 and 19 are a series of comparative top plan schematic diagrams illustrating the position of the X-ray tube relative to the same grids and orientations illustrated in FIGS. 13A, 14A, and 15A;

FIGS. 21A, 21B, 22A, 22B, 23A and 23B are a series of schematic diagrams illustrating the problem of image shifting during stereotactic imaging using the existing perpendicular stereotactic imaging geometry of a typical mammography apparatus with a collimating stainless steel needle biopsy compression paddle and a plurality of compact flat digital image receivers.

BEST MODE FOR CARRYING OUT THE INVENTION

Figure 1:
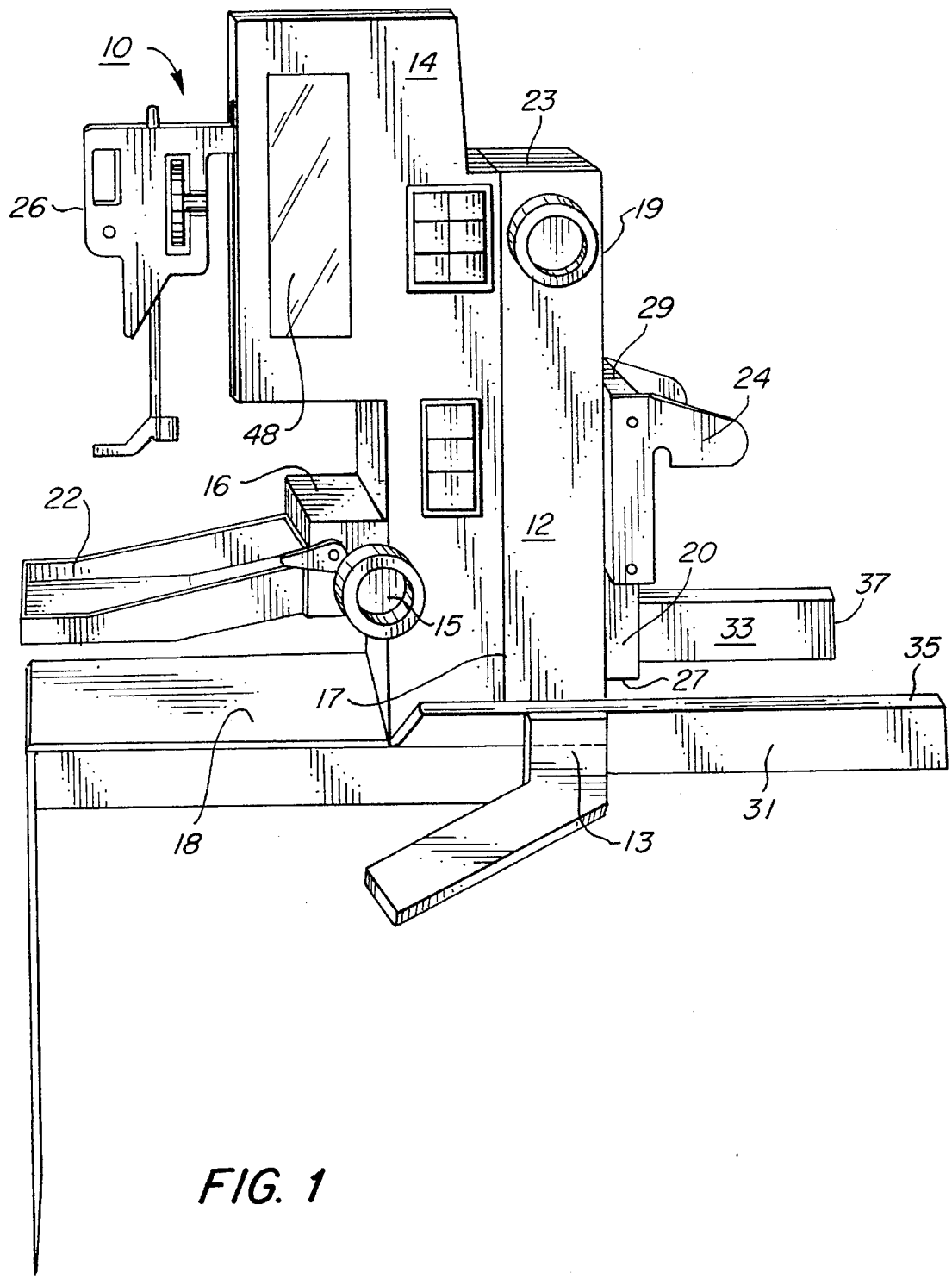
FIG. 1 is a side perspective view of the stereotactic needle biopsy apparatus of the present invention for converting a conventional mammography apparatus into a device for carrying out stereotactic mammographic guided needle breast biopsies.
Figure 2:
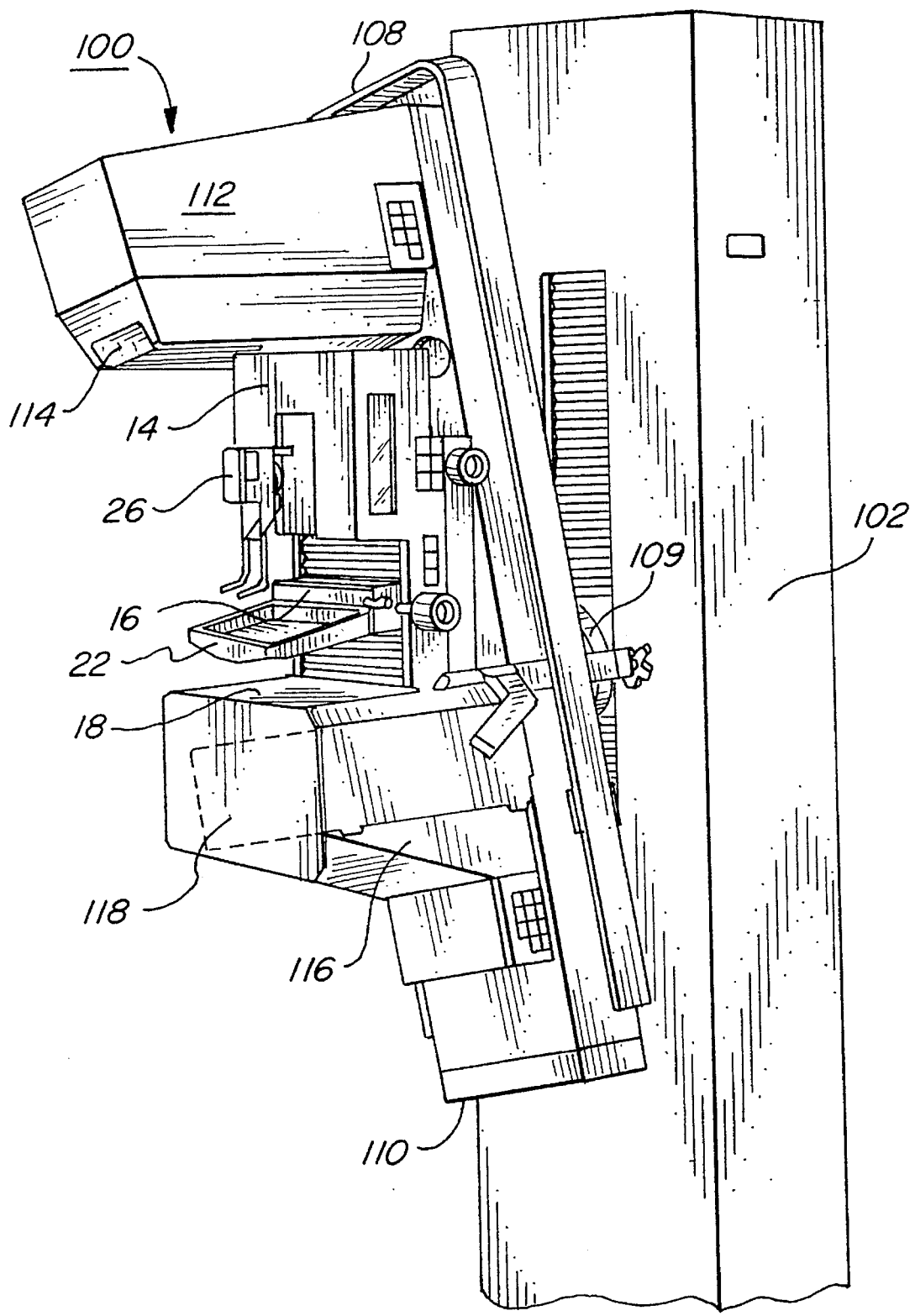
FIG. 2 is a side perspective view of a conventional mammography apparatus incorporating the stereotactic needle biopsy apparatus of the present invention.
Figure 3:
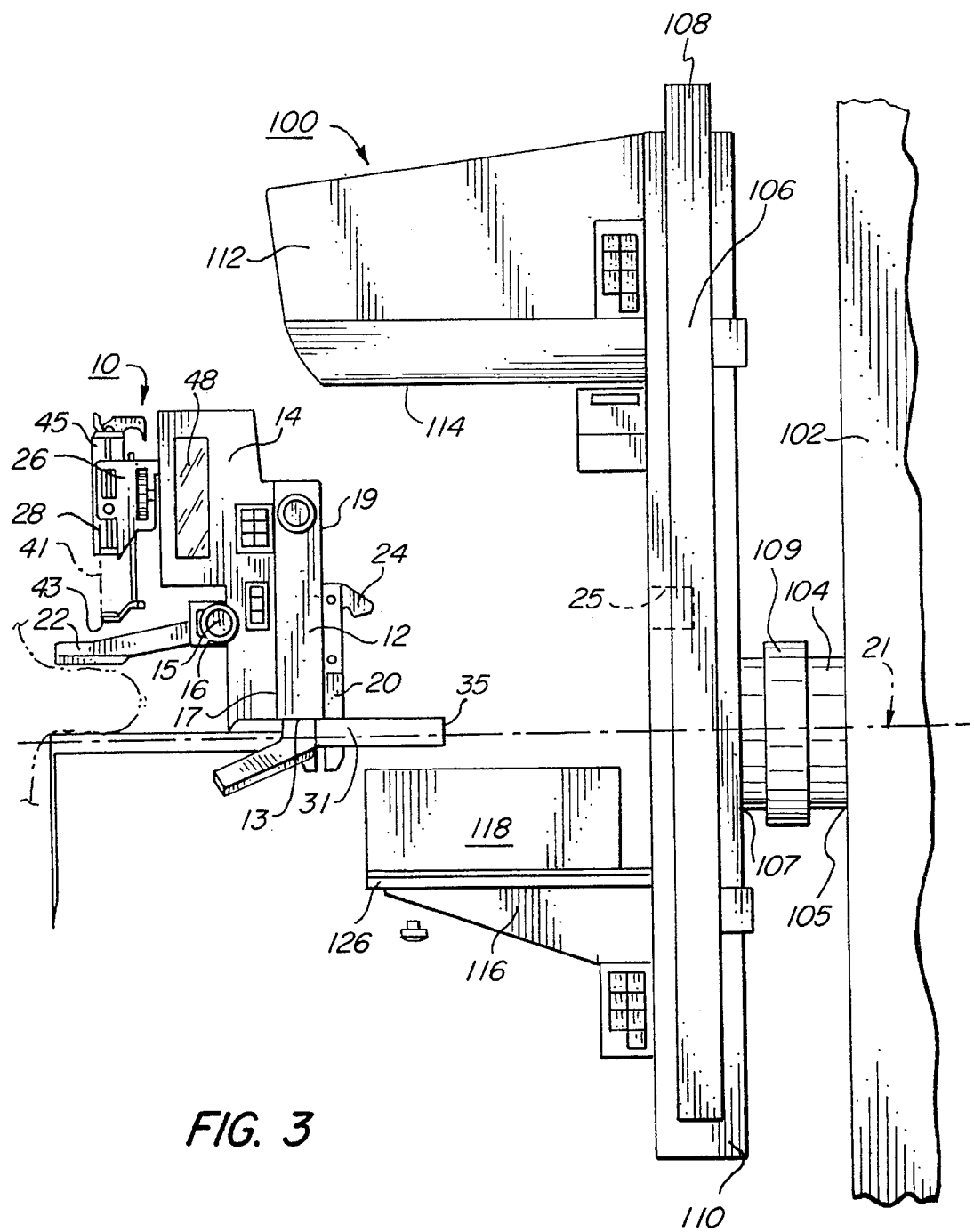
FIG. 3 is a side elevation view of the same conventional mammography apparatus incorporating the stereotactic needle biopsy apparatus of the present invention.

FIGS. 1, 2 and 3 primarily illustrate the preferred embodiment of the present invention. Referring to FIG. 1, there is generally shown an add-on stereotactic needle biopsy apparatus 10 which may be attached to a conventional mammography apparatus 100 to convert the mammography apparatus 100 into a device for performing stereotactic mammographic guided needle biopsies on a breast using the benefits of perpendicular stereotactic imaging geometry. The add-on apparatus 10 generally includes a base 12 having a first side 17 to which is attached an orthogonal three-dimensional needle guiding stage 14. The needle guiding stage 14 may utilize motors, if desired, to position the needle. The base 12 also has a compression plate engaging end 13 to which a compression plate 18 is affixed. Also, the base includes a compression paddle carriage 16 slidingly attached to the base 12 on its first side 17. Attached to the compression paddle carriage 16 is a stainless steel compression paddle 22 having an opening therein to permit a needle to pass through into a breast under compression. Compression paddle carriage 16 includes a knob 15 for manual movement of the compression carriage 16 along base 12. The compression paddle carriage may also include a motor for motorized sliding movement relative to the base 12. The biopsy apparatus also has a display window 48 for indicating the coordinates of the needle tip and the calculated coordinates of the lesion.

The biopsy apparatus 10 also includes a pivoting member 20 having a first end 27 and a second end 29. The first end 27 of the pivoting member is pivotally attached to a second side 19 of the base 12 near its compression plate engaging end 13. Stabilizing support arms 31 and 33 are affixed to the base 12 adjacent to its compression plate engaging end 13. Each of the stabilizing support arms 31 and 33 have ends 35 and 37 respectively which may be attached to the pivot shaft 104 of the mammography apparatus 100 via a collar 109 to aid with the affixation of the biopsy unit 10 thereto. Ends 35 and 37 of stabilizing support arms 31 and 35 secured to collar 109 provide a means for inhibiting the movement of the biopsy apparatus 10 during stereotactic X-ray imaging with the conventional mammography apparatus 100

Referring to FIGS. 2 and 3, the conventional mammography apparatus 100 generally includes a base 102, and a pivot shaft 104 having a first end 105 attached to the base 102 and a second end 107 which defines a pivot axis 21. The mammography apparatus 100 further includes an imaging arm 106 having an X-ray source end 108 and an X-ray receiving end 110. The second end 107 of the shaft 104 is attached to the imaging arm 106 between an X-ray source end 108 and an X-ray receiving end 110. The imaging arm 106 includes a pair of slots 25 positioned between the X-ray source end 108 and the X-ray receiving end 110. The slots 25 are shown as being offset from the pivot axis 21.

The mammography apparatus 100 further includes an X-ray tube head 112 having a focal spot 114 from which X-rays emanate. The X-ray tube head 112 is attached to the imaging arm 106 at the X-ray source end 108. An X-ray image receiver support 116 is attached to the imaging arm 106 at a point adjacent to the image receiving end 110. The image receiver support 116 provides a planar platform in which at least one edge of the plane is substantially perpendicular to the central ray emanating from the focal spot 114 of the X-ray tube 112. An image receiver 118 is mounted on the support 116 so as to present at least one edge of the associated image plane thereof perpendicular to the focal spot 114 of the X-ray tube head 112.

In FIGS. 2 and 3, X-ray image receiver 118 is illustrated as being a digital image receiver. FIG. 6A, for example, provides a schematic illustration of the principal components of the digital image receiver 118. The digital image receiver 118 generally includes a phosphor screen 120, a pellicle mirror 122, and a CCD camera 124 all enclosed in a light tight box 125. More specific details regarding the construction of the digital image receiver for mammographic imaging and processing digital mammographic images is described and shown in related U.S. Pat. No. 5,289,520. Alternatively, imaging can be accomplished using a standard mammography quality film-screen, similar or identical to that shown in related U.S. Pat. No. 5,289,520, together with X-ray scatter reducing grids.

Referring to FIGS. 1 and 3, the biopsy apparatus 10 also includes a pair of hooks 24 which are connected to the pivoting member 20. The hooks 24 provide a means for attaching the biopsy apparatus 10 to slots 25 on the image arm 106 mammography apparatus 100. In the preferred embodiment, pivoting member 20 on the biopsy apparatus 10 is attached to the image arm 106 via hooks 24, and pivoting member 20 allows the biopsy apparatus 10 to be angularly moved about the pivot axis 21 independent of the angular movement of the imaging arm 106 to which the pivoting member 20 is attached. This permits the imaging arm 106 to be positioned for stereotactic imaging while the breast is held stationary between the compression paddle 22 and the compression plate 18. Of course, imaging arm 106 and biopsy apparatus 10 can be positioned to perform a stereotactic needle breast biopsy procedure in any of the standard mammographic viewing positions such as the cranio-caudal or medio-lateral positions.

Still referring to FIGS. 1 through 3, the biopsy apparatus 10 further includes a removable needle holder 26 which is attached to the three dimensional needle guiding stage 14. The particular needle holder 26 illustrated in the figures is dimensioned to receive a biopsy gun 28 (shown in FIG. 3) to take core tissue samples of a breast. Other needle holder types, such as a holder for an aspiration needle or a holder for a localizing wire, may be employed without deviating from the spirit of the present invention.

In the preferred embodiment of the present invention, the needle holder 26 is attached to the three dimensional needle guiding stage 14 so that the axis of a biopsy needle 41, having needle sampling end 43 and needle holder engaging end 45, positioned therein is presented substantially normal to the plane formed by the fixed compression plate 18. In the preferred embodiment, the needle is moved in an orthogonal manner by the orthogonal needle guiding stage 14. Alternatively, the needle may be presented via a polar coordinate stage, such as that previously used by the TRC Mammotest. However, it is believed that the positioning of the needle tip using polar coordinates, rather than in the orthogonal coordinate system described above, is more difficult to visualize for the technician or user.

FIG. 6A generally illustrates the relative positioning of the X-ray tube focal spot 114, compression paddle 22 having an opening therein, compression plate 18 and a digital image receiver 118 for taking a non-stereotactic image with the biopsy apparatus 10 and mammography apparatus 100. FIGS. 5A and 7A generally illustrate the relative positioning of the focal spot 114, compression paddle 22, compression plate 18 and image receiver 118 during stereotactic imaging with the same biopsy apparatus 10 and mammography apparatus 100. As will be more fully explained below, one embodiment of the biopsy apparatus 10 of present invention includes features that make it compatible with a conventional mammography apparatus 100 equipped with a digital image receiver 118 so that images may be acquired in any of the positions illustrated in FIGS. 5A, 6A or 7A. Also, the biopsy apparatus 10 of the present invention is also fully compatible with the use of conventional film-screen image receivers and conventional scatter reducing grids typically used therewith.

Usually, the size and positioning of the phosphor screen 120, pellicle film 122, and CCD array in the CCD camera 124 of a digital image receiver 118 for a conventional mammography apparatus 100 are likely to have been optimized for taking non-stereotactic digital images, as shown in FIG. 6A. However, the size and positioning of these components may not necessarily be optimum for stereotactic imaging. As shown in FIGS. 5A and 7A, when the same digital image receiver is employed to take stereotactic images with an X-ray beam-collimating stainless compression paddle 22, the resulting X-ray images 121 tend to shift off of the phosphor screen 120 and out of the field of view of the CCD camera 124, as illustrated by a comparison of FIGS. 5B, 6B and 7B. The shifting phenomena occur because the focal spot 114 is moved relative to the stationary window in the stainless steel collimating compression paddle 22 causing the X-ray beam that passes through the window to be shifted about its central ray 200 from one stereotactic image to the other. This shifting results in the possibility that some of the image in the field of view of the CCD camera 124 may be lost because the image shifts off of the phosphor screen 120 which has been positioned to be in the field of view of the CCD camera 124 for conventional mammography. The amount of image loss generally depends on the thickness of the breast under compression.

The lost image problem associated with the shifting phenomena, as described above, can be solved by repositioning the image receiver 118 relative to the focal spot 114 for each of the stereotactic imaging positions. FIGS. 8A, 9A and 10A illustrate that by shifting the image receiver 118 a predetermined amount from the original position (shown in dotted lines) to a new position (shown in solid lines), the phosphor screen 120 can be aligned such that the compression paddle collimated stereotactic X-rays will fall onto the phosphor screen 120 completely within the field of view of the CCD camera 124 in each stereotactic imaging position. Movement of the image receiver 118 may be continuous or may be made in discrete steps. FIGS. 8B, 9B and 10B illustrate that the resulting X-ray images 121A, whether taken from the stereotactic positions as illustrated in FIGS. 8A or 10A, or taken from a centered or non-stereotactic position as illustrated in FIG. 9A, are properly aligned on the phosphor screen 120 so as to be within the field of view of the CCD camera 124.

Figure 20A:
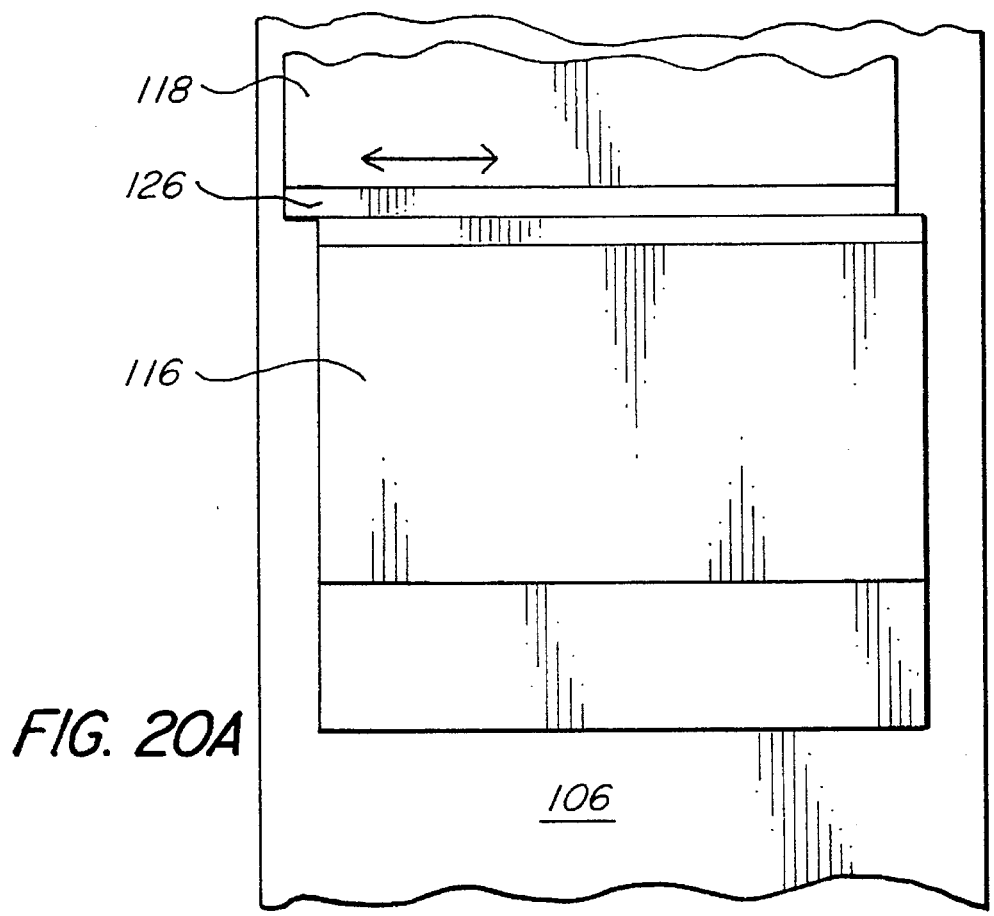
FIGS. 20A and 20B are side elevation schematic diagrams of the translation stage, affixed to the image receiver support, used to move the image receiver according to the present invention.
Figure 20B:
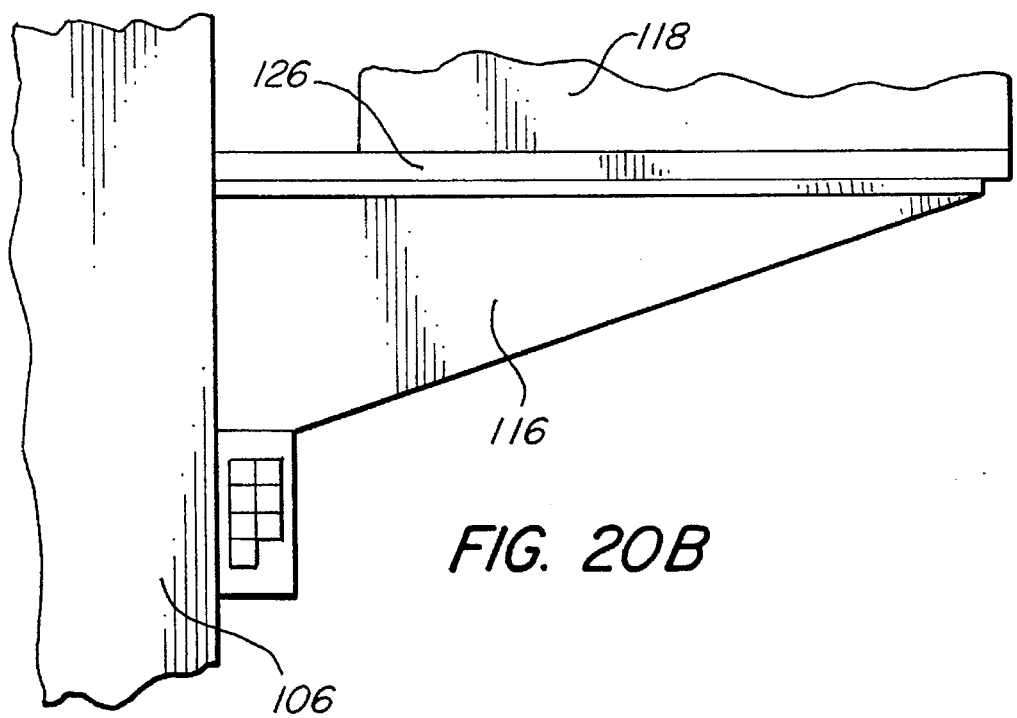

FIGS. 20A and 20B generally illustrate, by way of a schematic diagram, that repositioning of the image receiver 118 may be accomplished by affixing a translation stage 126 to the image receiver support 116 of the imaging arm 106 and thereafter affixing the X-ray image receiver 118 to the translation stage 126. Any translation stage providing movement in at least one direction is adequate for the purposes of the present invention. Those skilled in the art will appreciate that the positioning of a translation stage between the existing image receiver support 116 and the image receiver 118 can change the source-to-image distance (SID) of the mammography apparatus 100. Depending on the particular mammography apparatus used, some compensation or adjustment may be required to account for the change in SID of the existing mammography apparatus 100.

Alternatively, it should be appreciated by those skilled in the art that variations can be made to the above described apparatus to position the field of view of the CCD camera 124 relative to an X-ray image on a phosphor screen without departing from the spirit of the present invention. For example, if the phosphor screen 120 is made large enough so as to capture X-rays from each of the stereotactic imaging positions, then movement of the phosphor screen 120 with the translation stage is not needed. However, the CCD camera 124 and pellicle mirror 122 may still need to be moved to acquire the image from the phosphor screen 120. The camera 124 and the pellicle mirror 122 may be attached to translation stages within the light tight housing 125 and each may be moved separately or together relative to the phosphor screen 120 so that the field of view of the CCD camera 124 can be appropriately positioned relative to an image appearing somewhere on the phosphor screen 120.

Also, it should be appreciated by those skilled in the art that the digital image receiver 118 may be replaced with one or more flat panel digital image receivers which may occupy the position of the phosphor screen 120. One example of a known flat panel digital image receiver that may be used with the present invention is made from a sandwich configuration comprising a fiber optic face plate positioned between a scintillator and a CCD array. In such a configuration, X-rays impinging on the scintillator cause the scintillator to illuminate and the illumination of the scintillator is conducted by the fiber optic face plate to the CCD array where it is convened into stored electrical signals which may be read using conventional CCD array reading techniques.

Another example of a flat panel digital image receiver that may be used with the present invention comprises a radiation absorbing layer, such as amorphous selenium, sandwiched between an array of CMOS integrated circuits (pixel circuits) and a surface electrode layer transparent to the radiation. Each of the pixel circuits in the array has a charge collecting electrode. An external voltage applied between the surface electrode layer and the charge collecting electrodes produces an electric field across the thickness of the absorbing layer. When the panel is exposed to X-ray radiation, X-ray photons pass through the transparent surface electrode layer and are absorbed in the absorbing layer creating electron/hole pairs in the absorbing layer. A portion of the liberated electric charge migrates under the influence of the electric field toward the charge collecting electrodes which collect charge and store the charges in small capacitors located within each pixel circuit. This process results in a discrete distribution of stored voltages across the array proportional to the distribution of X-ray photons incident on the absorbing layers. Circuitry in each pixel provide for the voltage on each pixel capacitor to be recorded via readout circuitry and permits the resetting of the pixel capacitors.

FIGS. 21A through 23B illustrate the same image shifting problem when using a flat panel digital image receiver 150 during stereotactic imaging with the present invention. Similar to the CCD array used in the digital image receiver 118, the flat panel digital image receivers described above are usually limited in size. Thus, compensations must be made for the image shifting problem caused by the collimating stainless steel compression paddle 18 during stereotactic imaging. One method of compensation, similar to that described for the digital image receiver 118 of FIGS. 8A through 10B, is to proportionally reposition the flat panel digital image receiver 150 in the same manner used to reposition digital image receiver 118. Alternatively, flat panel image receiver 150 may comprise a plurality of flat panels 152, 154 and 156 arranged such that X-ray images created by the three general imaging positions shown in FIGS. 21A, 22A and 22A, fall on flat panels 156, 154, and 152 respectively.

Now referring to FIGS. 11A, 11B, 12A and 12B, the repositioning of the image receiver 118 is proportional to the thickness of the compressed breast being imaged. As shown in the figures, relatively thin compressed breasts require less repositioning of the image receiver during stereotactic imaging than relatively thick compressed breasts. This is simply a result of the amount of X-ray collimation performed by the stainless steel compression paddle 22 and opening therein. As the paddle 22 gets closer to the compression plate 18 and hence closer to pivot axis 21 aligned therewith, the image is shifted less. Thus, less repositioning of the image receiver 118 is required to get the image on the phosphor screen 120 and ultimately within the field of view of the CCD camera 124 because the resulting stereotactic image is shifted less (FIG. 11B) than the resulting stereotactic image of a thicker breast (FIG. 12B). FIGS. 11C and 12C are generally cross sectional views of the thin and thick breast illustrating the imageable and, thus needle biopsy accessible volume, therein with the present invention. In each breast, the imageable and accessible volume of the breast narrows from the compression paddle 22 to the compression plate 18. It is one aspect of the present invention to provide a biopsy apparatus which provides the maximum accessible volume of breast tissue close to the entry point of the biopsy needle through the opening in the compression paddle 22. Some prior art devices may actually have the maximum accessible volume of breast tissue at a point furthest away from the compression paddle opening. In other words, the V or cone shaped access areas indicated by dotted lines 134 and 136 may actually appear inverted with the oblique angle stereotactic imaging geometry. In the event that a lesion is determined in a lower region of a breast near the compression plate 14

Figure 4:
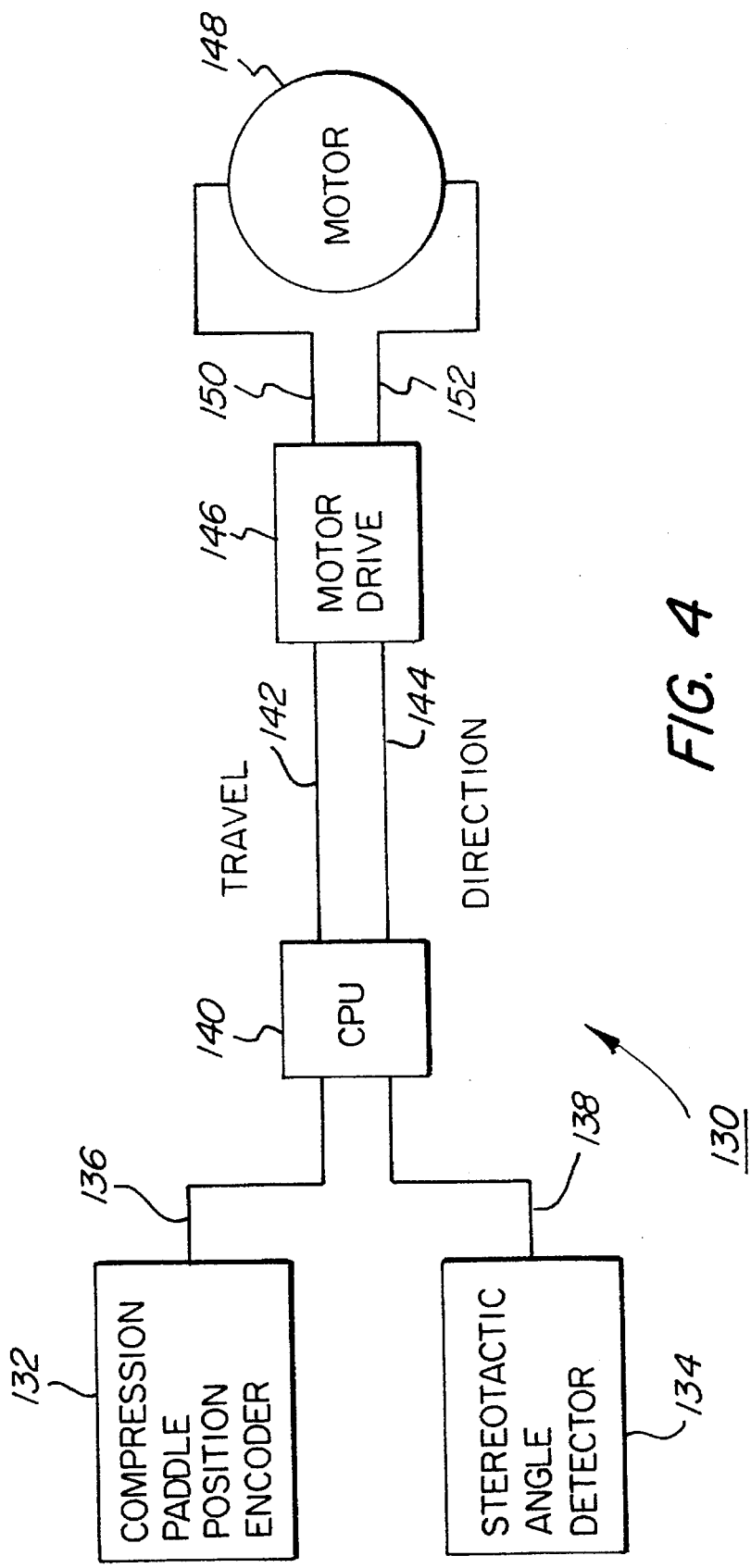
FIG. 4 is block diagram of the control system for controlling the digital image receiver shifting motor.

To accomplish proportional repositioning of the image receiver 118 automatically during stereotactic imaging, the present invention is provided with a image receiver positioning control system 130 shown in FIG. 4. According to the present invention, the compression paddle carriage 16 is fitted with a position encoder 132 to indicate the position of the carriage 16 and compression paddle 22 relative to the fixed compression plate 18. Pivot member 20 is fitted with a stereotactic angle detector 134, which may comprise a limit switch or a position encoder, to indicate the particular stereotactic viewing angle selected relative to the fixed compression plate 18. Outputs of the compression paddle carriage position encoder 132 and stereotactic angle detector 134 are fed via lines 136 and 138 to a central processing unit (CPU) 140, which calculates the amount and direction that the image receiver 118 must be moved to align an image within the field of view of the CCD camera 124. The calculations made by the CPU are based on the dimension of the window in the collimating stainless steel compression paddle, the size of the CCD camera field of view and the distance between the compression paddle and the film plane. Once direction and amount values are calculated, the CPU 140 provides travel and direction output instructions via lines 142 and 144 to a translation stage motor drive 146 which in turn controls translation stage motor 148 via lines 150 and 152 to move stage 126 to the appropriate position as determined by the CPU 140. Obviously, movement of the translation stage 126 is performed once the breast has been compressed by the compression paddle 22 and the X-ray tube 112 has been moved to a stereotactic imaging position. CPU 140 may control the translation stage 126 to move the image receiver 118 in a continuous fashion or in discrete steps, as desired.

If desired, the biopsy apparatus 10 may be conveniently used with a conventional film-screen image receiver, rather than a digital image receiver 118. Furthermore, in contrast to the prior art devices described in U.S. Pat. No. 4,727,565, and the Bolmgren article, apparatus 10 may be used with conventional image optimizing apparatus and techniques such as a moving scatter reducing grid. Conventional moving scatter reducing grid that can be employed with the present invention is marketed by Smit Roentgen as model 9896.010.05291. This grid has 31 lines per centimeter, having a grid ratio of 5 to 1, with a focal film distance of 65 centimeters. The Smit Roentgen grid is equipped with means for moving the grid laterally during an X-ray exposure. The advantages of being able to use perpendicular stereotactic imaging geometry with the apparatus 10 over the disadvantages of the oblique angle stereotactic imaging geometry employed by the prior art can best be seen by reference to FIGS. 13A through 19. In such cases where a film-screen image receiver is used, the conventional moving scatter reducing grid is positioned between the X-ray source and the image receiver.

Figure 13A:
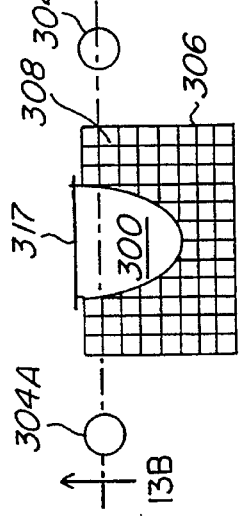
FIG. 13A is top plan schematic diagram illustrating the relationship of the X-ray absorbing materials of a cross-pattern scatter reducing grid to the X-ray tube position during stereotactic imaging with the prior art devices employing oblique angle stereotactic imaging geometry.
Figure 13B:
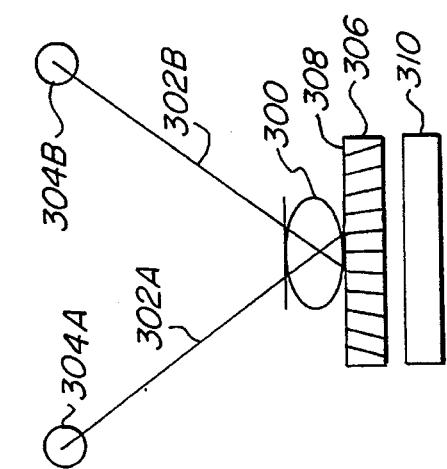
FIG. 13B is a cross-sectional front elevation diagram of the structure shown in FIG. 13A taken along the line 13B illustrating the position of the X-ray tube relative to the film plane and X-ray absorbing materials of the cross-pattern scatter reducing grid.

Referring to the schematic illustrations of FIGS. 13A and 13B, there is shown the results of an attempt to stereotactically image a breast 300 using a prior art apparatus such as that described in U.S. Pat. No. 4,727,565 with a scatter reducing grid having a plurality of focused planar X-ray absorbing materials arranged in a cross pattern and inclined such that the plurality of planes are aligned with the focal spot of the X-ray tube. Primary, information containing X-rays emanating from the focal spot 304A, which are nearly parallel to central ray 302A, cannot pass through cross grid 306 to reach the X-ray film-screen 310 because substantially all of the primary X-rays are absorbed by the X-ray absorbing material 308. The same may be said for the primary X-rays, nearly parallel to central ray 302B, emanating from X-ray focal spot 304B in the other stereotactic position. No matter which way the scatter reducing cross-pattern grid 306 is planarly rotated relative to the image receiver, the cross-pattern grid 306 cannot be focused at the X-ray focal spot 304A, 304B during stereotactic imaging. Thus, a cross-pattern grid 306 cannot be used in any conventional manner with the prior art devices employing oblique angle imaging geometry to obtain stereotactic X-ray images.

Figure 14A:
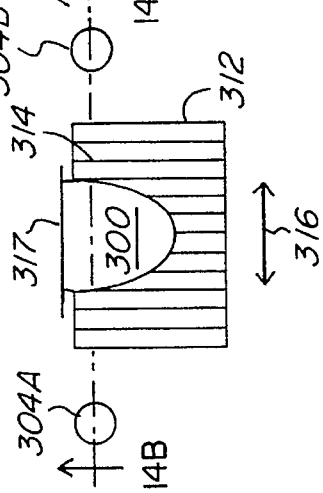
FIG. 14A is a top plan schematic diagram illustrating the relationship of the X-ray absorbing materials of a conventional linear scatter reducing grid oriented in a conventional manner to the X-ray tube position during stereotactic imaging with the prior art devices employing oblique angle stereotactic imaging geometry.
Figure 14B:
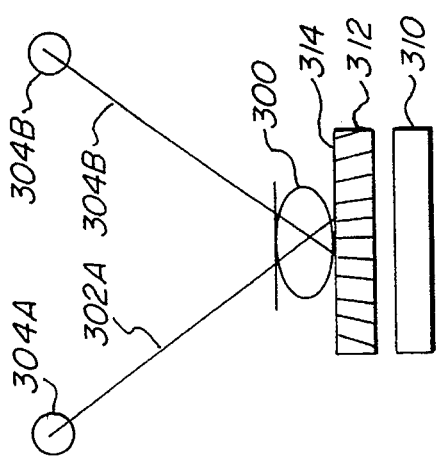
FIG. 14B is a cross-sectional front elevation diagram of the structure shown in FIG. 14A taken along the line 14B illustrating the position of the X-ray tube relative to the film plane and X-ray absorbing materials of the conventional linear scatter reducing grid oriented in the conventional manner.

Referring to the schematic illustrations of FIGS. 14A and 14B, there is shown the results of an attempt to stereotactically image the breast 300 using the same apparatus as described in U.S. Pat. No. 4,727,565 with a conventional mammography grid 312 having a plurality of focused X-ray absorbing planar slats 314, sometimes referred to as lamellae. In such conventional grids 314, the planar slats are often inclined slightly such that the plane of each slat is substantially aligned with the focal spot of the X-ray tube. As with the cross-pattern grid 306 of FIGS. 13A and 13B, the primary X-rays emanating from focal spot 304A, 304B in either stereotactic position cannot reach the film-screen 310 because the planar slats 314 of the grid 312 absorb substantially all of the X-rays. Normally, during conventional mammography procedures, the X-ray grid 312 is moved slightly during the X-ray exposure in a direction, shown by arrow 316, which is tangential to a patient's chest wall 317 to blur out shadows cast by the planar slats 314. As those skilled in the art will appreciate, the tangential movement 317 allows the benefits of the moving grid 312 to be employed close to the patient's chest wall 317. However, with the prior art device using oblique angle imaging geometry, this orientation of the grid cannot be used.

Figure 15A:
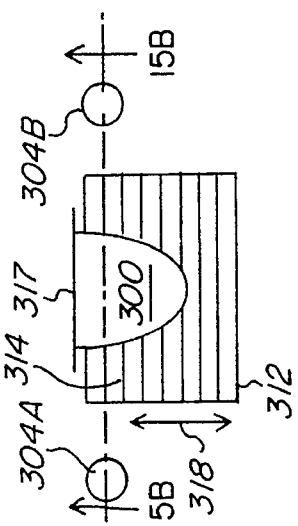
FIG. 15A is a top plan schematic diagram illustrating the relationship of the X-ray absorbing materials of a conventional linear scatter reducing grid oriented in an unconventional manner to the X-ray tube position during stereotactic imaging with the prior art devices employing oblique angle stereotactic imaging geometry.
Figure 15B:
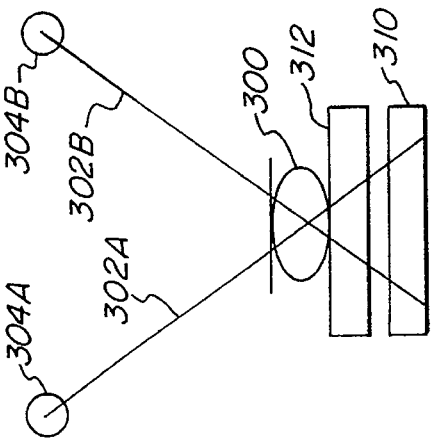
FIG. 15B is a cross-sectional front elevation view of the structure shown in FIG. 15A taken along the line 15B illustrating the position of the X-ray tube relative to the film plane and X-ray absorbing materials of the conventional linear scatter reducing grid oriented in the unconventional manner.

FIGS. 15A and 15B illustrate the only orientation for the conventional scatter reducing grid 312 that may be used with the prior art devices. While this orientation would allow X-rays to reach the film-screen 310 and would permit movement of the grid 312 in the direction shown by arrow 318 to blur the shadows cast by the planar slats 314, this orientation of the grid is not the preferred orientation in mammographic imaging because the movement direction does not allow the benefits of moving the grid 312 to be utilized close to the chest wall 317 of the patient because the chest wall 317 can impede the movement of the grid 312.

The difficulties encountered by the prior art devices when combined with scatter reducing grids, such as 306 and 312 are overcome by the biopsy apparatus 10 of the present invention because the focal spot 114 is always within the focus of the grids. Referring to exemplary schematic illustrations of FIGS. 16A through 16C, it can be seen that by rotating the film screen 310 and grid 312 with the focal spot during stereotactic imaging, the slats 314 of the grid remain substantially pointed or focused at the focal spot 114. Thus, primary, information containing X-rays emanating from the focal spot 114 can reach the film screen 310 substantially unimpeded.

FIGS. 17, 18 and 19 further illustrate that no matter what stereotactic image position is used, the focal spot 114 remains in the same position relative to the grids 306 and 312 irrespective of the orientation of the grid. Therefore, the grids 306 and 312 may be moved in all the directions shown in arrows 316–322 during imaging, and preferably, such grids can be moved in the conventional manner which is substantially tangential to the patient's chest wall. Also, the biopsy apparatus 10 of the present invention, unlike the prior art, will not impede the use of a cross pattern on a grid 306 that is oriented in an offset manner, such as that described in U.S. Pat. No. 2,605,427, so that the shadows cast by the X-ray absorbing materials 308 can be blurred by using one directional motion such as that shown by arrow 320 tangential to the chest wall 317.

After the breast has been stereotactically imaged with the biopsy apparatus 10 and mammography apparatus 100 of the present invention to obtain two stereotactic images of the breast, the three dimensional coordinates of a suspicious lesion shown in each of the images can be determined according to the particular method described in related grandparent U.S. Pat. No. 5,289,250, starting at Column 9, Line 16. Once the three dimensional coordinates are determined, the needle guiding stage 14 is used to position the needle tip in the suspicious lesion wherein a sample of the lesion may be taken.

While the present invention provides numerous benefits to stereotactic imaging, including the ability to use a conventional moving scatter reducing grid in a conventional manner, as well as using a digital image receiver for stereotactic imaging, the present invention also provides an additional benefit of enabling the image receiver to be located some distance from the breast such that there is a gap between the breast and the image receiver. This gap results in an increase in the contrast of X-ray images because the gap reduces the number of scattered X-rays that reach the image receiver.

It will thus be seen that the objects and advantages set forth above and those made apparent from the preceding descriptions, are efficiently attained and, since certain changes may be made in the above construction without departing from the scope of the invention, it is intended that the matter contained in the above description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. An apparatus for performing stereotactic mammographic needle biopsies on a breast, the apparatus comprising:
   a base;
   a pivot shaft having a first end attached to the base and a second end, the pivot shaft further defining a pivot axis;
   an imaging arm having an X-ray source end and an X-ray receiving end, the imaging arm being attached to the second end of the pivot shaft at a point between the X-ray source end and the X-ray receiving end;
   an X-ray tube having a focal spot, the X-ray tube being connected to the imaging arm at its X-ray source end;
   an X-ray image receiver support affixed to the imaging arm at its X-ray receiving end;
   an X-ray image receiver attached to the support; and
   a removable needle biopsy apparatus further comprising:
   a biopsy apparatus base having a first side, a second side and a compression plate engaging end,
   a compression plate attached to the biopsy apparatus base at the compression plate engaging end, the compression plate further defining a compression plate plane,
   a multi-dimensional positionable biopsy needle guiding stage attached to the biopsy apparatus base on its first side,
   a biopsy needle holder attached to the needle guiding stage,
   a compression paddle carriage slidably attached to the biopsy apparatus base on its first side between the biopsy needle guiding stage and the compression plate engaging end,
   a compression paddle, having an opening therein permitting a biopsy needle to be inserted into a breast, attached to the compression paddle carriage,
   a pivot member having first and second ends, wherein the first end of the pivot member is attached to the second side of the biopsy apparatus base near its compression plate engaging end, the pivot member allowing pivotal motion of the biopsy apparatus base relative to the imaging arm about the pivot axis defined by the pivot shaft; and
   means for attaching the biopsy apparatus to the imaging arm, the means being affixed to the pivot member at its second end.

2. The apparatus of claim 1, wherein the X-ray image receiver supported by the X-ray image receiver support is a film-screen.

3. The apparatus of claim 2, wherein the apparatus further comprises an X-ray scatter reducing grid having a plurality of planar X-ray absorbing materials, and wherein the X-ray scatter reducing grid is positioned between the compression plate and the film-screen.

4. The apparatus of claim 3, wherein the apparatus further comprises means for moving the X-ray scatter reducing grid laterally during a stereotactic X-ray exposure in a direction tangential to a patient's chest wall so as to blur shadows cast on the film screen by the X-ray absorbing materials of the scatter reducing grid.

5. The apparatus of claim 2, wherein the apparatus further comprises an X-ray scatter reducing grid having a plurality of planar X-ray absorbing materials arranged in a cross pattern, and wherein the X-ray scatter reducing grid is positioned between the compression plate and the film-screen.

6. The apparatus of claim 5, wherein the apparatus further comprises means for moving the X-ray scatter reducing grid laterally during a stereotactic X-ray exposure in a direction tangential to a patient's chest wall so as to blur shadows cast on the film screen by the X-ray absorbing materials of the scatter reducing grid.

7. The apparatus of claim 1, wherein the apparatus further comprises a digital X-ray receiver having a phosphor screen and a CCD camera having a field of view on at least a portion of the phosphor screen,
   means for predicting the location of an X-ray image on the phosphor screen; and
   means for positioning the field of view of the CCD camera relative to the predicted location of an X-ray image appearing on the phosphor screen.

8. The apparatus of claim 1, wherein the apparatus further comprises:
   an image receiver translation stage, the translation stage being attached to the X-ray receiver support at the image receiving end of the imaging arm;

a digital X-ray image receiver comprising a light tight housing, a phosphor screen within the light tight housing, and a CCD camera having a field of view focused at the phosphor screen within the light tight housing, wherein the digital X-ray image receiver is affixed to the image receiver translation stage; and wherein the biopsy apparatus further comprises:

means for indicating the position of the compression paddle carriage relative to the fixed compression plate;

means for indicating the stereotactic X-ray image angle relative to the compression plate plane; and means for moving the translation stage relative to the image receiver support and X-ray tube focal spot so as to position the phosphor screen of the digital image receiver relative to an X-ray beam's central ray, the means being electrically connected to the means for indicating the position of the compression paddle carriage and the means for indicating the stereotactic X-ray angle.

9. A removable stereotactic needle biopsy apparatus for attachment to a mammography apparatus, the removable biopsy apparatus comprising:

a biopsy apparatus base having a first side, a second side and a compression plate engaging end;

a compression plate attached to the biopsy apparatus base at the compression plate engaging end;

a biopsy needle guiding stage attached to the biopsy apparatus base on its first side;

a biopsy needle holder attached to the needle guiding stage;

a breast compression paddle carriage slidably attached to the biopsy apparatus base on its first side between the biopsy needle guiding stage and the compression paddle;

a pivot member having a first and second end, wherein the first end of the pivot member is attached to the second side of the biopsy apparatus base near its compression plate engaging end, the pivot member allowing pivotal motion of the biopsy apparatus base relative to an imaging arm of a mammography apparatus about a pivot axis adjacent to the second end of the pivot member; and means for attaching the biopsy apparatus to an imaging arm of a mammography apparatus, the means being affixed to the pivot member at its second end.

* * * * *